United States Patent
Hage et al.

(10) Patent No.: US 6,500,671 B2
(45) Date of Patent: Dec. 31, 2002

(54) LOADING MICROCOLUMS FOR THE SEPARATION OF ANALYTES FROM A SAMPLE IN THE MILLISECOND TIME SCALE

(75) Inventors: David S. Hage, Lincoln, NE (US); William A. Clarke, Baltimore, MD (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 15 days.

(21) Appl. No.: 09/776,800

(22) Filed: Feb. 5, 2001

(65) Prior Publication Data

US 2002/0146840 A1 Oct. 10, 2002

(51) Int. Cl.⁷ .................................................. G01N 30/56
(52) U.S. Cl. .................... 436/161; 73/61.53; 210/198.2; 210/656; 436/178; 436/183
(58) Field of Search .................... 436/161, 178, 436/183; 210/656, 198.2; 73/61.53

(56) References Cited

U.S. PATENT DOCUMENTS

| | | | |
|---|---|---|---|
| 4,351,909 A | * | 9/1982 | Stevens |
| 5,174,959 A | * | 12/1992 | Kundu et al. |
| 5,595,653 A | | 1/1997 | Good et al. |
| 5,599,677 A | | 2/1997 | Dowell et al. |
| 5,605,839 A | * | 2/1997 | Simpson et al. |
| 5,800,692 A | * | 9/1998 | Naylor et al. |
| 5,863,401 A | | 1/1999 | Chen |
| 6,225,132 B1 | | 5/2000 | Drukier et al. |
| 6,080,590 A | | 6/2000 | Van Der Greef et al. |
| 6,261,848 B1 | | 7/2000 | Anderson et al. |

OTHER PUBLICATIONS

Ageev et al. Derwent Acc. No. 1995–059579. SU 1832194 (Aug. 7, 1993).* de Alwis et al., Rapid Heterogeneous Competitive Electrochemical Immunoassay for IgG in the Picolmole Range, *Anal. Chem.*, Dec. 1987, pp. 2786–2789, vol. 59, No. 23, Amer. Chem. Society.

Cheng et al., Bovine Serum Albumin Adsorption and Desorption Rates on Solid Surfaces with Varying Surface Properties, *J. Coll. Inter. Sci.*, Jul. 1987, pp. 212–223, vol. 118, No. 1, Academic Press, Inc.

Dombrowski et al., Investigation of Anion–Exchange and Immunoaffinity Particle–Loaded Membranes for the Isolation of Charged Organic Analytes from Water, May 1998, pp. 1969–1978 vol. 70, Amer. Chem. Society.

Fernando et al., Investigation of the Kinetic Properties by Particle–Loaded Membranes for Solid–Phase Extraction by Forced Flow Planar Chromatography, *Anal. Chem.*, Mar. 1993, pp. 588–595, vol. 65, No. 5, Amer. Chem. Society.

Hage et al., High–Performance Immunoaffinity Chromatography and Chemiluminescent Detection in the Automation of a Parathyroid Hormone Sandwich Immunoassay, *Anal. Chem.*, Mar. 1991, pp. 586–595, vol. 69, Amer. Chem. Society.

(List continued on next page.)

*Primary Examiner*—Jan Ludlow
(74) *Attorney, Agent, or Firm*—Senniger, Powers, Leavitt & Roedel

(57) ABSTRACT

The present invention generally relates to a microcolumn capable of separating an analyte from a sample in the millisecond time domain. The microcolumn is capable of such rapid separation by employing small column volumes that can tolerate medium to high flow rates. The invention also relates to a method of loading a microcolumn capable of separating an analyte from a sample in the millisecond time domain using plural injections of the packing material.

20 Claims, 9 Drawing Sheets

OTHER PUBLICATIONS

Hage et al., Theory of a Sequential Addition Competitive Binding Immunoassay Based on High–Performance Immunoaffinity Chromatography, *Anal. Chem.*, Jun. 1993, pp. 1622–1630, vol. 65, Amer. Chem. Society.

Hage, Immunoassays, *Anal. Chem.*, Jun. 1993, pp. 420R–424R, vol. 65, No. 12, Amer. Chem. Society.

Hage et al., Split–Peak Affinity Chromatographic Studies of the Immobilization–Dependent Adsorption Kinetics of Protein A, *Anal. Chem.*, Feb. 1986, pp. 274–279, vol. 58, Amer. Chem. Society.

Hage, Survey of recent advances in analytical applications of immunoaffinity chromatography, *J. Chrom.*, Sep. 1998, pp. 3–28, vol. 715, No. 1, Elsevier Science B.V.

Hage et al., Development of a Theoretical Model for Chromatographic–Based Competitive Binding Immunoassays with Simultaneous Injection of Sample and Label, *Anal. Chem.*, Aug. 1999, pp. 2965–2975, vol. 71, No. 15, Amer. Chem. Society.

Hagen et al., Membrane approach to solid–phase extractions, *Anal. Chim. ACTA*, 1990, pp. 157–164, vol. 236, Elsevier Science Publishers B.V.

Janis et al., Dual–Column Immunoassays Using Protein G Affinity Chromatography, *Anal. Chem.*, Sep. 1989, pp. 1901–1906, vol. 61, Amer. Chem. Society.

Karamushka et al., Kinetics Of Sorption Immobilization Of Serum Albumin On Silicopolymethyl–siloxane, *Appl. Chem.*, Mar. 1989, pp. 561–564, vol. 62, No. 3, Plenum Publishing Corporation.

Larsson, High–Performance Liquid Affinity Chromatography, *Enz. Purification & Related Tech.*, 1984, pp. 212–223, vol. 104, Academic Press, Inc.

Lok et al., Protein Adsorption on Crosslinked Polydimethylsiloxane Using Total Internal Reflection Fluorescence, Jan. 1983, pp. 104–116, vol. 91, No. 1, Academic Press, Inc.

Norde et al., Streaming Potential Measurements as a Tool to Study Protein Adsorption Kinetics, *J. Colloid Inter. Sci.*, Oct. 1990, pp. 169–176, vol. 139, No. 1, Academic Press, Inc.

Ohlson et al., High–Performance Liquid Affinity Chromatography: Rapid Immunoanalysis of Transferrin in Serum, *Clin. Chem.*, 1988, pp. 2039–2043, vol. 34, No. 10, Amer. Assoc. for Clin. Chem.

Place et al., Split–Peak Phenomenon in Nonlinear Chromatography. 2. Characterization of the Adsorption Kinetics of Proteins on Reversed–Phase Supports, *Anal. Chem.*, Jul. 1991, pp. 1222–1227, vol. 63, Amer. Chem. Society.

Podgornik et al., High–Performance Membrane Chromatography of Small Molecules, *Anal. Chem.*, Aug. 1999, pp. 2987–2991, vol. 71, No., 15, Amer. Chem. Society.

Pollema et al., Flow Injection Renewable Surface Immunoassay: A New Approach to Immunoanalysis with Fluorescence Detection, *Anal. Chem.*, Jun. 1994, pp. 1825–1831, vol. 66, No. 11, Amer. Chem. Society.

Ramsden et al., Protein Adsorption Kinetics Drastically Altered by Repositioning a Single Charge, *J. Amer. Chem. Soc.*, Aug. 1995, pp. 8511–8516, vol. 117, No. 33, Amer. Chem. Society.

Rollag et al., Analysis of Pesticide Degradation Products by Tandem High–Performance Immunoaffinity Chromatography and Reversed–Phase Liquid Chromatography, *Anal. Chem.*, 1996, pp. 3631–3637, vol. 68, No. 20, Amer. Chem. Society.

Thomas et al., Determination of Atrazine in Water Using Tandem High–Performance Immunoaffinity Chromatography and Reversed–Phase Liquid Chromatography, *Anal. Chem.*, 1994, pp. 3823–29, vol. 66, No. 21, Amer. Chem. Society.

Van Dulm et al., The Adsorption of Human Plasma Albumin on Solid Surfaces, with Special Attention to the Kinetic Aspects, *J. Colloid Inter. Sci.*, Jan. 1983, pp. 248–255, vol. 91, No. 1, Academic Press, Inc.

Voegel et al., Adsorption Kinetics of Plasma Proteins Onto Silica, *Coll. & Surf.*, Aug. 1984, pp. 9–19, vol. 10, Elsevier Science Publishers B.V.

Young et al., Protein Adsorption on Polymeric Biomaterials, *J. Colloid Inter. Sci.*, Sep. 1988, pp. 246–260, vol. 125, No. 1.

Zhou et al., Membrane Supports as the Stationary Phase in High–Performance Immunoaffinity Chromatography, *Anal. Chem.*, Jan. 1999, pp. 115–118, vol. 71, No. 1, Amer. Chem. Society.

Clarke et al., Development of Sandwich HPLC Microcolumns for Analyte Adsorption on the Millisecond Time Scale, Anal. Chem., Mar. 2001, pp. 1366–1373, vol. 73, No. 6, Amer. Chem. Society.

Clarke et al., Analysis of Free Drug Factions by Ultrafast Immunoaffinity Chromatogarphy, Anal. Chem., May 2001, pp. 2157–2164, vol. 73, No. 10, Amer. Chem. Society.

\* cited by examiner

LOADING MICROCOLUMS FOR THE SEPARATION OF ANALYTES FROM A SAMPLE IN THE MILLISECOND TIME SCALE

FIELD OF THE INVENTION

The current invention is generally directed toward a microcolumn and a method of loading a microcolumn. The microcolumn produced by the method of the invention is capable of separating an analyte from a sample in the millisecond time scale by using small column volumes that can tolerate medium to high flow rates.

BACKGROUND OF THE INVENTION

One area of continuing interest in the field of analytical chemistry is the development of separation techniques that achieve extraction of an analyte from a sample in the millisecond time domain. The ability to rapidly and accurately separate analytes from a sample has a number of important applications in the health, pharmaceutical, clinical, research and environmental fields. One such application, for example, is the ability to rapidly extract the biologically active form of a drug, hormone, or toxin from a biological sample. This is of particular interest in clinical chemistry and pharmaceutical science as a means for controlling and studying the effect of drugs and/or hormones within the body.

Techniques such as microbore HPLC and capillary HPLC have attempted to decrease separation times and increase separation efficiency by decreasing column diameter with a corresponding increase in column length. The small column diameter acts to decrease column volume, while the increased column length serves to provide more contacts between the analyte and the separation medium. Although these techniques have increased separation efficiency by obtaining narrower elution peaks, they have not resulted in separations in the millisecond time domain.

In another approach, some techniques have attempted to decrease extraction time by reducing column lengths. Many HPLC-based immunoaffinity columns are now in the size range of a few millimeters to a few centimeters. However, columns with these dimensions, while separating an analyte from a sample in a few seconds, cannot achieve separation in the millisecond time domain. Additionally, membrane supports based on polymeric materials that are several millimeters to several centimeters in diameter and several millimeters in length have been developed. However, like the immunoaffinity columns previously discussed, the membrane supports are not capable of separating an analyte from a sample in the millisecond time domain.

Accordingly, a need exists for a column with dimensions that are capable of achieving a high rate of selective separation in the millisecond time domain.

SUMMARY OF THE INVENTION

Among the several aspects of the invention therefore, is provided a method of loading a microcolumn comprising an active layer and an inert layer, the active layer being capable of separating an analyte from a sample, the method comprising introducing the active layer into the microcolumn such that the active layer is capable of separating the analyte from the sample within the millisecond time domain, and introducing the inert layer.

Another aspect of the invention is provided a microcolumn for separating an analyte from a sample, the microcolumn comprising an active layer capable of separating the analyte from the sample in the millisecond time domain, and an inert layer.

In yet a further aspect is provided a method for separating an analyte from a sample in the millisecond time domain, the method comprising applying the sample to the microcolumn described herein.

BRIEF DESCRIPTION OF THE DRAWINGS

These and other features, aspects, and advantages of the present invention will become better understood with regard to the following description, appended claims and accompanying figures where:

ABBREVIATIONS AND DEFINITION

To facilitate understanding of the invention, a number of terms and abbreviations as used herein are defined below:

"Analyte" or "Target Analyte" are used interchangeably herein, and shall mean the component of the sample to be separated by the active layer of the microcolumn.

"Binding Agent", as utilized herein, shall mean the agent in the active layer capable of separating the target analyte from the sample.

"Millisecond Time Domain or Millisecond Time Scale" are used interchangeably herein, and shall mean any amount of time less than one second.

"Sandwich microcolumn", as utilized herein, shall mean an embodiment of the invention wherein the microcolumn comprises a top inert layer, a bottom inert layer and an active layer between the two inert layers.

"Sample" or "Liquid" are used interchangeably herein and shall mean the mixture applied to the microcolumn containing the analyte. In addition to the analyte, the sample (liquid) generally also comprises a loading buffer. Any loading buffer may be employed to the extent that the buffer does not interfere with the separation process.

"Uniform Manner", as utilized herein, shall mean loading the layers of the microcolumn in a manner such that these layers have a substantially equal distribution of support in both a horizontal and vertical direction.

BSA=Bovine Serum Albumin

FPLC=Fast-Protein Liquid Chromatography

HPLC=High-Performance Liquid Chromatography

DESCRIPTION OF THE PREFERRED EMBODIMENTS

Applicants have discovered a new class of microcolumns that allows separation of an analyte from a sample in the millisecond time scale. The microcolumns achieve such rapid separation by employing a thin active layer comprising support particles that are capable of tolerating medium to high flow rates and pressures during sample injection, in combination with a small column volume. Applicants have also discovered a method of loading a microcolumn in layers to obtain a uniform, thin active layer by utilizing a plurality of injections to load the column. This provides column dimensions that are especially suitable for very rapid separation of an analyte from a sample. In addition, because of the small column volumes, the microcolumn also advantageously employs very small amounts of support particles. This is advantageous because it generally decreases the cost of column construction.

Figure 9:
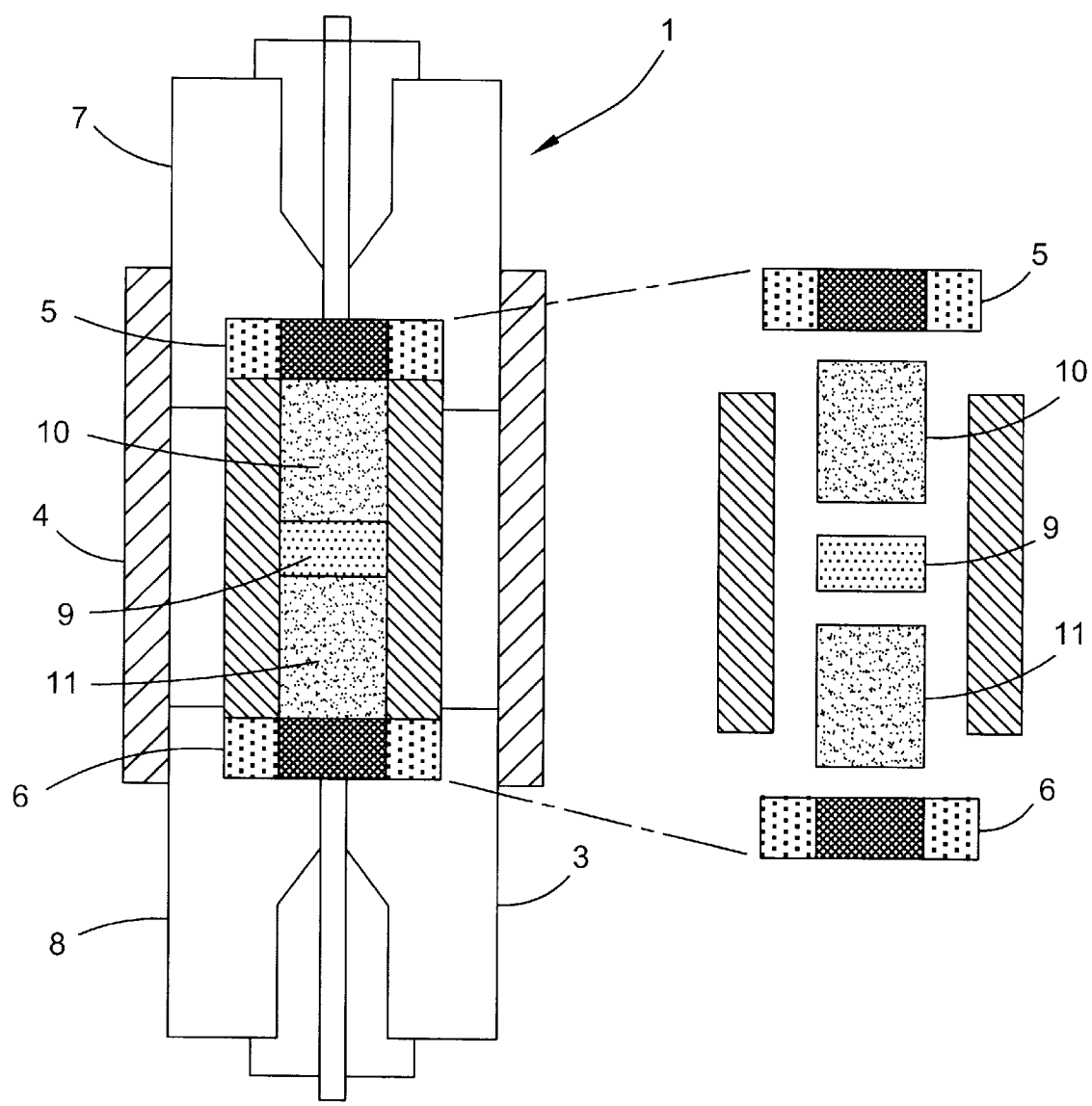
FIG. 9 depicts a drawing of a typical microcolumn according to the present invention.

As utilized herein, the terms "microcolumn" or "column" are used interchangeably and FIG. 9 depicts a typical microcolumn of the invention. As shown in FIG. 9, the microcolumn 1 generally has a tubular configuration with a first end 2, a second end 3, a passageway 4 there between, and a retaining means at the first 5 and second ends 6 of the microcolumn 1. However, the microcolumn 1 may comprise any number of different shapes, all of which are embodiments of the present invention. The retaining means 5, 6 typically comprises a mesh or small-pore material that acts to hold the support particles within the column while allowing fluid flow there through. The microcolumn 1 may also contain end fittings at the first 7 and second 8 ends of the microcolumn 1 used to connect the column to the chromatographic system. The microcolumn 1 comprises a thin active layer 9 to facilitate separation of the analyte from the sample in the millisecond time scale and typically a single inert layer in one embodiment, to several inert layers in additional embodiments. FIG. 9 illustrates an embodiment with a top inert layer 10 and a bottom inert layer 11.

Figure 1:
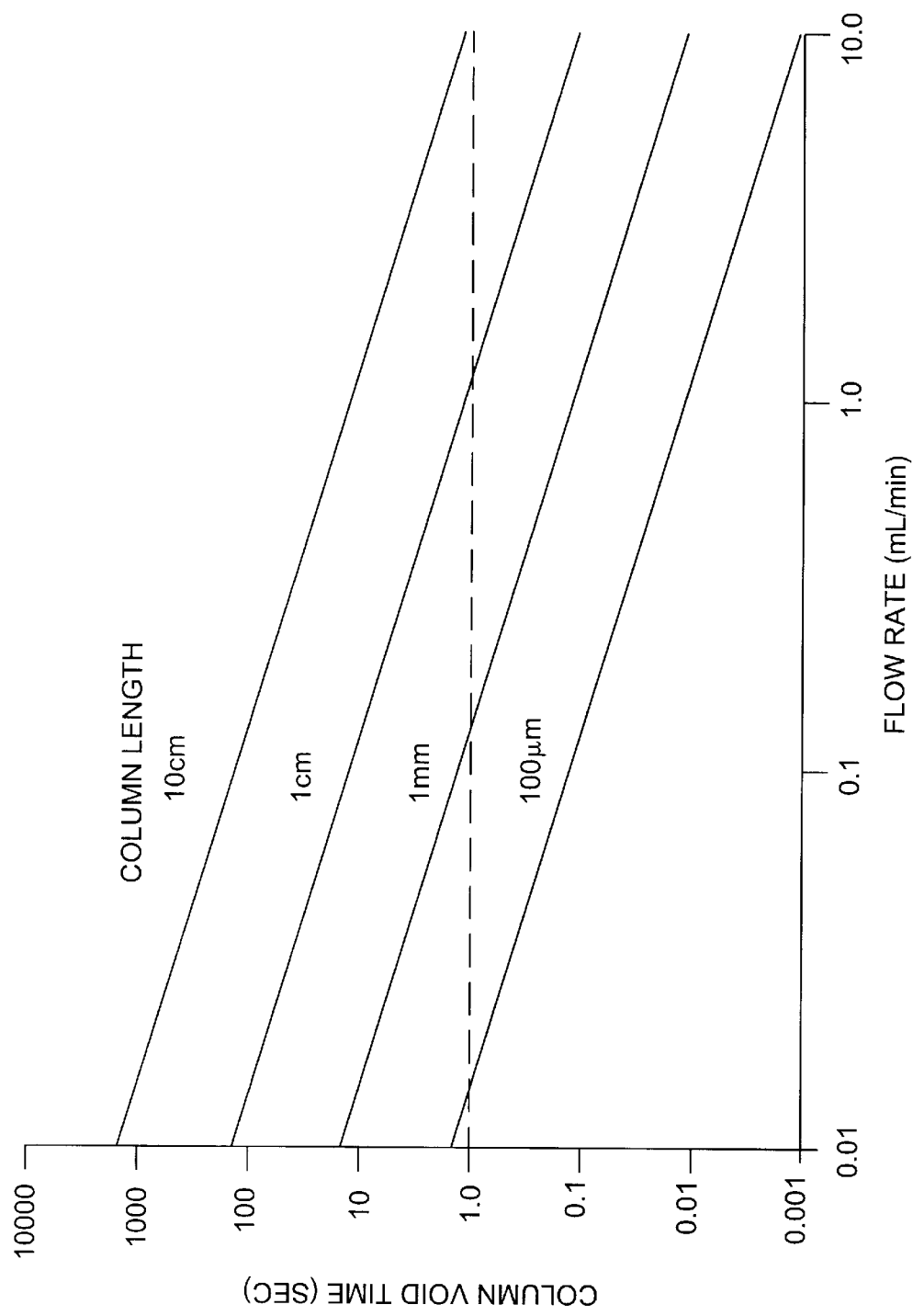
FIG. 1 depicts change in column void time with column length and solvent flow rate for 2 mm ID HPLC columns packed with porous silica. These results assume an overall porosity of 0.80 within the column (i.e., 80% of the column volume is occupied by the mobile phase). Using a column with an inner diameter of 1 mm or 4 mm gives similar results but with the vertical position of the lines in this graph being lowered or raised by 4-fold, respectively.

The microcolumn of the present invention is particularly suitable for separation of an analyte from a sample in the millisecond time scale because of its relatively thin active layer. As utilized herein, "length" of a layer means the thickness or width of the layer. FIG. 1, is a plot (derived by calculation) showing how the void time for an HPLC column will change as the length of the column and solvent flow rate are varied. As illustrated by FIG. 1, only column lengths in the size range of about 100 microns to about 1 millimeter or less allow separation in the millisecond time domain when employing standard HPLC flow rates of about 0.1 to about 1.0 mL/min. Accordingly, in order to facilitate millisecond separation, the microcolumns of the present invention comprise an active layer that may be less than about 10 microns in thickness. Typically, however, the active layer is from about 10 microns to about 1.1 millimeters in thickness and preferably, is not less than approximately 60 microns in thickness. Applicants have found that active layers with these dimensions, depending upon the particular application, are typically capable of extracting an analyte in about 1 to about 500 milliseconds. More preferably, the analyte is separated from the sample in less than about 200 milliseconds.

In addition to rapid extraction of the analyte, the microcolumn of the invention is typically capable of separating the target analyte with a high degree of selectivity. The microcolumn, in a particularly preferred embodiment, also has a relatively high binding affinity for the target analyte. The active layer, therefore, typically comprises support particles derivatized with any binding agent possessing the desired selectivity. For a separation based upon immunoaffinity, the binding agents are antibodies raised against the target analyte. The antibodies can be either monoclonal or polyclonal. However, monoclonal antibodies are generally employed in applications where a higher degree of selectivity is desired and polyclonals are more typically utilized in applications where a higher degree of binding affinity is desired. Examples of other suitable binding agents for affinity chromatography include nucleic acid ligands (e.g. aptamers), synthetic molecular imprints, antibody fragments (e.g. Fab fragments), antibody related molecules (e.g. chimeras or $F_v$ chain fragments), and recombinant proteins that act as antibody mimics. Typical support particles for affinity layers include antibodies adsorbed to a Protein G Nucleosil Si-1000 (Macherey-Nagel) support or any other support generally known to immobilize antibodies. For a separation that is based on reversed phase chromatography, a support that contains a hydrophobic binding agent, such as C18 Nucleosil Si-100 (Marcherey-Nagel), or any other support generally known may be employed. In addition, for a separation that is based upon ion-exchange chromatography, the active support particles may contain anionic or cationic groups on their surfaces. The binding agent, once selected, may be isolated in accordance with any generally known method.

The binding agent, if applicable, can be derivatized to the support particles by any method generally known in the art.

However, the method preferably immobilizes the binding agent to the support particle in a manner such that a relatively high percent of the binding agent is active (i.e. binds the target analyte) after the immobilization process. Suitable immobilization methods, for example, include the Schiff base method and the carbonyldiimidazole method. The Schiff base method is generally employed when immobilizing the binding agent through free amine groups. However, when the binding agent comprises antibodies, applicants have found that a more preferred approach is immobilization through the antibodies' carbohydrate region because this generally results in an active layer with a higher number of active binding sites compared to when immobilization is performed through free amine groups. Any method known in the art for immobilization via carbohydrate regions may be employed.

Additionally, the overall binding capacity of the microcolumn is also an important feature, particularly when the column is employed in methods such as affinity chromatography, because it impacts both the time and efficiency of extraction by the active layer. The binding capacity of the column, in part, is determined by the number of active binding sites present in the active layer. Preferably, the minimum number of active binding sites in the column comprises a ratio of active binding sites to free analyte not less than about 1:1, and more preferably, not less than about 10:1. However, even more preferably, support particles in the active layer will be derivatized with the maximum concentration of active binding agent possible so that the column has the largest binding capacity possible.

The active layer, additionally, may comprise a number of different support particles. The support particles, as detailed above, function primarily as a surface to immobilize the binding agent within the active layer. The diameter of the particle, however, is a feature that should be considered because it impacts both the length of the active layer and the amount of binding agent that may be immobilized in the active layer (i.e. binding capacity of the column). Preferably, the particle size is smaller than the length of the desired active layer. Applicants have found that a preferred particle diameter is less than about 10 times to about 20 times the length of the active layer because particles within this size range facilitate uniform packing of the layer. Because, applicants have found, that a particle diameter about 10 to about 20 times less than the active layer thickness allows for a better opportunity for small defects in the individual support layers to average out and produces a more uniform cross-section for this layer. In addition, the support particles should be able to tolerate the flow rates and pressures needed in order to obtain the desired sample contact time with the active layer. The properties that affect the pressure and flow rate that may be tolerated by the support particles include the diameter of the particle, the particle's shape and the porosity of the particles. Suitable support particles include porous or nonporous glass, silica and other inorganic supports (e.g., alumina or zirconia), carbohydrate-based supports (e.g., beaded agarose), and polymeric supports (e.g., polymethacrylate or polystyrene based resins); however, one generally skilled in the art of chromatography can select other appropriate support particles.

The microcolumn will typically comprise a single inert layer or several inert layers, depending upon the application. However, common features shared by all inert layers, irrespective of their number or position within the microcolumn, are that they generally should have no substantial interaction with the desired analyte, and should preferably, be mechanically stable under the flow rate and pressures employed during the separation process. Preferable materials for construction of the inert layer include diol-bonded silica, diol-bonded glass beads, agarose beads, hydroxylated perfusion media, and glycol coated perfusion media. The various inert layers may be constructed from the same support particles or different support particles. However, it is usually preferred for the sake of convenience in loading the microcolumn, that the inert layers comprise the same support particles.

The layers in the microcolumn may comprise either an active layer alone, or an active layer and a single inert layer on top of the active layer (wherein the active layer is in communication with the second end retaining means) such that liquid first passes through the inert layer and then passes through the active layer. The utilization of a single inert layer in this manner is especially suitable for applications where the liquid (containing the sample) is to be applied in only a single direction to the active layer and the column. The inert layer in this application preferably occupies the entire length of the microcolumn between the beginning of the first end of the microcolumn to the beginning of the active layer so that the entire microcolumn is filled with support particles. Applicants have found that having the entire microcolumn filled with support particles increases both the speed and efficiency of separation. Additionally, the inert layer in this application also preferably acts to distribute the injected sample evenly across the diameter of the column before the sample reaches the active layer. This allows for a more uniform application of the sample to the relatively thin active layer.

The layers in the microcolumn may also comprise an active layer between a top and a bottom inert layer. As utilized herein, the term "top inert layer" shall mean the layer that liquid first passes through prior to reaching the active layer and "bottom inert layer" shall mean the layer where liquid passes after it exits the active layer. The microcolumn preferably comprises both a top and bottom inert layer for applications where liquid is to be applied in two direction to the active layer and the column. At any given time, the flow of liquid through the column is generally only in a single direction. However, for example, it is sometimes preferable to alternate the flow of liquid through the column in order to help wash out any impurities that may have built up at the top of the column during the application of liquid. The top inert layer in this embodiment serves the same role as discussed above for the application employing a single inert layer e.g. more efficient separation. However, applicants have found that it is preferable to include the bottom inert layer, even in applications where fluid flow is in only in a single direction, because its inclusion increases the useful life of the active layer by preventing loss of active support particles.

The length of the inert layer is not a critical feature and does not affect the time needed to separate an analyte from the sample. In general, as stated above, the top inert layer (if present) is preferably the length that remains between the beginning of the column and the beginning of the active layer. And, the bottom inert layer, if it is present, is generally from about 1 to about 5 times the length of the active layer. Typically, the top inert layer is thicker than the bottom inert layer.

The choice of a particular type of housing for the microcolumn is also not a critical facet. The microcolumn housing, however, preferably employs components made of materials that are substantially inert to biological fluids and in particular, substantially inert to the analyte so as not to interfere with the separation process. Accordingly, any material that is substantially inert may be employed to construct the microcolumn. Suitable materials include stainless steel, polypropylene, certain plastics (such as PEEK which is a polymer (polyetheretherketone) and is provided in the form of HPLC tubing, frits and other HPLC components by Upchurch Scientific and fused silica.

The dimensions of the microcolumn are also not a critical feature. Any size of microcolumn may be utilized to the extent that the total column length is preferably greater than the length of the active layer. The total column length and diameter also typically allow the use of sufficiently fast flow rates and pressures to achieve the desired contact time between the sample and the active layer. Preferably, the microcolumn has an internal diameter of about 50 microns to about 2 centimeters and a length of about 0.2 millimeters to about 2 centimeters. In a particularly preferred embodiment, the microcolumn has an internal diameter of about 0.5 to about 2.1 millimeters and a length of about 1 millimeter to about 2 centimeters.

Applicants have found that thin active layers may be obtained by loading the support particles comprising the layer into the microcolumn via a plurality of injections, as described in more detail below (e.g. see FIG. 3). The normal method of loading a column, applying the support particles in one application to the column with the amount of support particles being in excess of that which is needed to fill the column, is sufficient for standard size chromatography columns because due to their size, reliable packing of the support particles may be achieved. Applicants, however, have found that loading the support particles in a single injection, for columns with dimensions described herein, generally does not result in an active layer capable of reproducibly achieving separation of an analyte from a sample in the millisecond time scale.

Accordingly, the layers are preferably loaded into the column by a plurality of injections of slurry comprising the support particles. The slurry may be injected into the column employing any apparatus generally known for injecting a slurry into a column, for example, a closed-loop sample application system with either a manual injection valve or an automatic injection system. The slurry, in addition to support particles, also preferably comprises a packing solvent or buffer. The packing solvent employed to load the slurry into the column is not a critical feature; however, the solvent preferably will not harm the binding agent present in the active layer. One skilled in the art of chromatography can readily select both an appropriate apparatus to inject the slurry and appropriate packing solvents.

Figure 3:
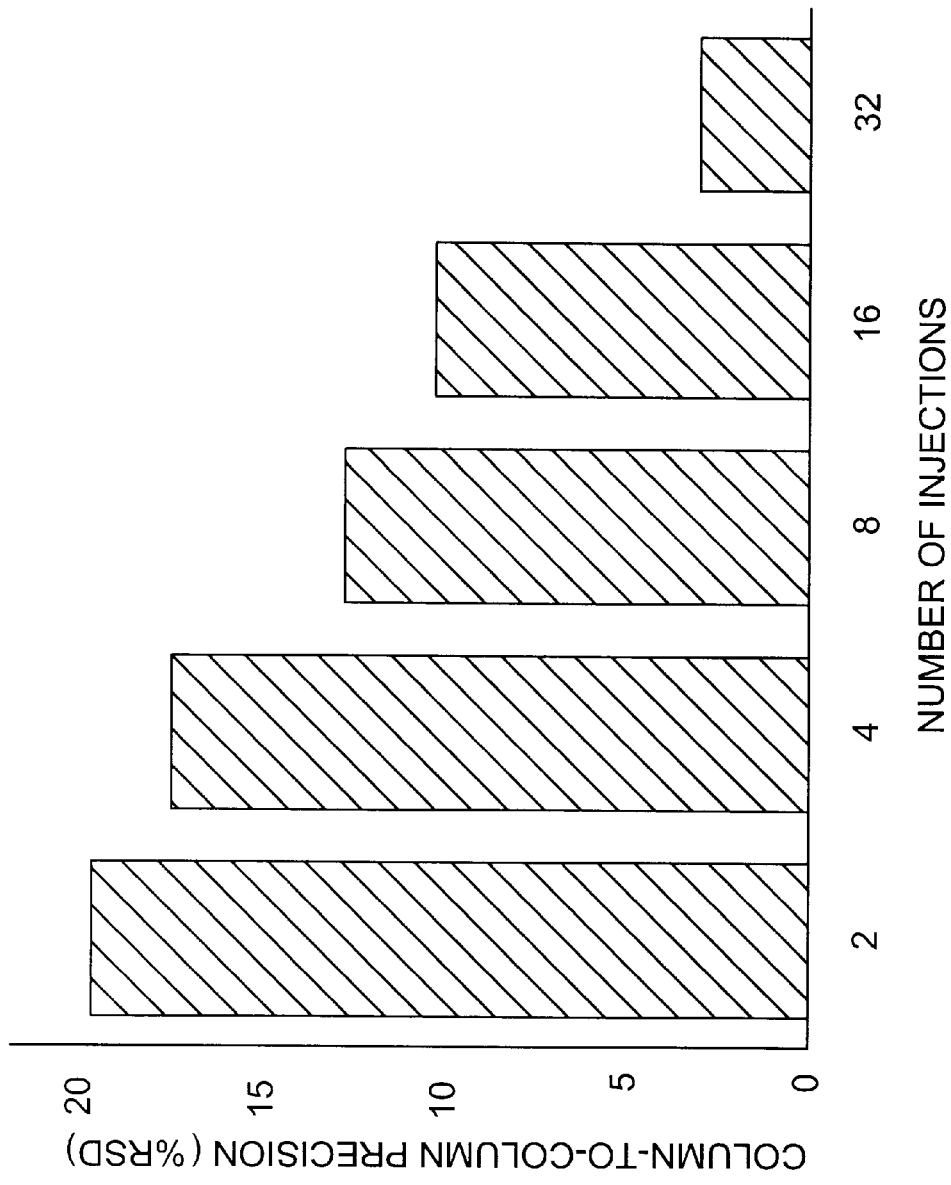
FIG. 3 depicts the reproducibility of stationary phase content in a microcolumn as a function of the number of injections which were used to apply to fixed amount of an immobilized hemoglobin support to a 2.1 mm ID×620 $\mu$m microcolumn. These results represent the average result of triplicate analyses.

Applicants have also found, as illustrated by FIG. 3, employing a larger number of injections and less support per injection, achieves a more controlled delivery of support particles because statistical variations that occur during the delivery of small amounts of support particles to the column are averaged out. This is particularly true as layer thickness decreases. Uniform packing of support particles in the layers, especially the active layer, is preferable because it provides more reproducible results for injected samples by allowing parts of the sample that are injected at different locations along the diameter of the column to achieve consistent sample contact times with the active layer. Accordingly, the number of injections to introduce a layer into the column is generally from about 10 to about 100. More preferably, the number of injections to introduce a layer is from about 30 to about 40 when the layer length is from about 100 to about 500 microns, and is from about 60 to about 80 injections when the layer length is from about 60 to about 100 microns in length.

The slurry density (milligrams of support particles per milliliter of packing solvent), or amount of support particle applied to the column per injection, will vary greatly depending upon the desired thickness of the layer. Typically, however, the slurry density will be from about 0.1 to about 20 milligrams of support particles per milliliter of packing solvent and more preferably, will be from about 1 to about 5 milligrams of support particles per milliliter of packing solvent. In general, the inert layer(s) and active layer are loaded at approximately the same slurry density. The volume of slurry injected per application (injection) may also be varied as a means to control layer thickness. Typically, the volume of slurry injected per each application is about 50 $\mu$l to about 300 $\mu$l. One of ordinary skill in the art can readily determine the appropriate slurry density and volume per injection needed to achieve a layer having a particular thickness when employing a specific number of injections. For example, equation 2 set forth in the examples section provides one means to determine the slurry density to achieve a particular layer thickness when loading the layer into the column by a plurality of injections.

The desired slurry density, once selected, is preferably maintained throughout column injection in order to facilitate uniform layer packing. To maintain consistent slurry density, the slurry typically undergoes shaking between injections to ensure that the support particles are uniformly distributed in the slurry. It is also preferable to monitor the turbidity of the slurry at a wavelength of approximately 800 nm to ensure the amount of support particles per milliliter remains constant. Furthermore, typically the slurry density is calculated at numerous points during injection by comparison to slurries of known density employing the same support particles.

Applicants have also found, in addition to loading the support particles by a plurality of injections, that varying the flow rate and pressure during column loading also serves to provide a more stable and well-defined active layer (and inert layer). In a particularly preferred application, the pressure and flow rate are increased for a short period of time near the beginning and end of the loading of each layer. This increased pressure and flow rate facilitates compression of the layer and distributes the layer evenly across the diameter of the column. In a typical column loading procedure, for example, the flow rate of slurry injection into the column is between about 3 mL/min and about 5 mL/min, with the higher flow rate occurring generally at the beginning and end of the loading of each layer. Additionally, pressure during column loading is typically maintained between about 2000 and about 4000 psi, with a higher pressure preferably occurring at the beginning and end of the loading of each layer. The particular flow rates and pressures utilized to load each layer of the column is not a critical feature and accordingly, may be varied significantly from the general examples provided herein depending upon the particular application.

Table 1 sets forth a general procedure for loading a 1.0 cm immunoaffinity microcolum employing a layer design comprising an active layer between a top and bottom inert layer. The procedure set forth in Table 1 is for illustrative purposes only and shall not be construed to limit the scope of the present invention as described in greater detail herein.

TABLE 1

General Procedure for Preparing a Microcolumn

| | |
|---|---|
| 1 | Assemble column fittings on the second end of the microcolumn (and retaining means) and attach the microcolumn to the packing apparatus; |
| 2 | Make two particle support slurries in the packing solvent, one consisting of inert support particles, and the other containing the active support particles. For an immunoaffinity microcolumn, the packing solvent employed may be pH 7.0, 0.10M potassium phosphate buffer and the slurry of the inert support particles typically may contain a diol-bonded material (e.g. 2 mg/mL diol-bonded silica). The second slurry contains the immunoaffinity support particles at a concentration that is determined by utilizing equation 2 or any other generally known method (as set-forth in the examples below) and the desired thickness of the final active layer |
| 3 | Begin flow of the packing solvent through the column. This is generally done at a rate of approximately 3 mL/min for immunoaffinity microcolumns, but is not critical. Make approximately five injections (at 150 µl per injection for a 1.0 cm long column) of the inert support slurry, followed by an increase in flow rate to approximately 5 mL/min for approximately 5 minutes |
| 4 | Return the flow rate to approximately 3 mL/min and make the required number of injections of the active layer (per equation 2 or any other generally known method). After making these injections, increase the flow rate to approximately 5 mL/min for approximately 5 minutes |
| 5 | Return the flow rate to approximately 3 mL/min and make enough injections of the inert support slurry to fill the remainder of the column bed |
| 6 | After the column bed has been filled, increase the column backpressure to the desired level, typically about 3000 to about 4000 psi. Allow the column to equilibrate at this pressure for at least 30 minutes. Gradually release the pressure. Remove the column from the packing apparatus and place a frit (retaining means) and end fitting onto the open end of the column. The column is now ready for use |

The microcolumn, in addition to its relatively thin active layer, is also generally able to tolerate flow rates and pressures during sample injection that are capable of achieving the desired sample contact time with the active layer. The flow rate and pressure selected depends not only on the support particles employed in its layer construction, but also on the column diameter and upper pressure limit that can be tolerated by the chromatographic system. In general, any flow rate and pressure necessary to achieve the desired residence time and tolerated by the chromatographic system employed is within the scope of the present invention. Typically, however, the microcolumns of the present invention may be subjected to flow rates of between about 0.01 to about 9.0 mL/min and pressures between about to about 6000 psi. More preferably, the pressure is between about 100 to about 1500 psi.

The microcolumns of the present invention may be employed in any separation system and are particularly suitable for applications in which short residence times or rapid extractions are desired. Accordingly, the columns may be used in any type of liquid chromatography including HPLC, FPLC, and ultra high-pressure chromatography. These categories preferably include, but are not limited to affinity chromatography, immunoaffinity chromatography, reversed-phase chromatography, normal phase chromatography, adsorption chromatography, ion exchange chromatography, chiral chromatography, capillary electrochromatography, and solid-phase extraction or microextraction methods. The columns may also be employed in gas chromatography and/or supercritical fluid chromatography. In a preferred embodiment, the columns are employed in HPLC systems because these systems facilitate flow rates and residence times that are preferable when utilizing the microcolumns described herein.

In addition, the microcolumns of the present invention may be utilized to separate any analyte from a sample. Accordingly, in one embodiment the microcolumns may be employed to extract an analyte from a biological sample, such as the biologically active form of a drug or hormone from a blood sample. Additionally, the analyte may comprise a protein, bacteria or fragment thereof, viral particle, toxin or environmental agent. Encompassed in another embodiment, the microcolumns are used in clinical sensors for the real-time monitoring of drugs, hormones or other biological agents during surgery or in an emergency room. Another embodiment encompasses the use of the microcolumns for real-time monitoring and feedback control of biochemical reactors, such as to generate biotechnological products. In yet another embodiment, is encompassed the use of the microcolumns in high-throughput screening, where a large number of samples must be processed (e.g. screening the interaction of large protein libraries with specific biological agents for use in proteomics). Additionally, the microcolumns may be employed for sample pretreatment or handling as part of miniaturized separation and analysis systems, such as those based upon capillary electrophoresis or capillary electrochromatography.

The detailed description set-forth above is provided to aid those skilled in the art in practicing the present invention. Even so, this detailed description should not be construed to unduly limit the present invention as modifications and variation in the embodiments discussed herein can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

Without further elaboration, it is believed that one skilled in the art can, using the preceding description, utilize the present invention to its fullest extent. The following preferred specific embodiments are, therefore, to be construed as merely illustrative, and not imitative of the remainder of the disclosure in any way whatsoever.

EXAMPLES

The examples illustrate the ability of the microcolumns of the present invention to extract an analyte from a sample in the millisecond time range under both adsorption and diffusion-limited conditions. The examples also illustrate that the microcolumns are able to achieve such rapid extraction when used under typical HPLC flow rates and pressure conditions.

Materials and Methods

Reagents. The bovine hemoglobin, bovine serum albumin (BSA), fluorescein isothiocyanate (FITC)-labeled BSA, mouse anti-BSA antibodies and mouse anti-fluorescein antibodies were from Sigma (St. Louis, Mo.). Sodium fluorescein was obtained from Matheson, Coleman and Bell (Cincinnati, Ohio). Reagents for the bicinchoninic acid (BCA) protein assay were purchased from Pierce (Rockford, Ill.). HPLC-grade Nucleosil Si-1000 (7 μm particle diameter, 1000 Å pore size) and Nucleosil $C_{18}$ Si-100 (5 μm particle diameter, 100 Å pore size) were obtained from Alltech (Deerfield, Ill.). All other chemicals were reagent-grade or better and were used without further purification. All aqueous solutions were prepared using deionized water from a Nanopure water system (Barnstead, Dubuque, Iowa).

Apparatus. All columns were packed using a CM3200 pump from Thermoseparations (Riviera Beach, Fla.) and a modified Valco N60 six-port valve (Houston, Tex.). Prior to packing, the support slurries were kept in suspension by a Thermolyne Rotomix 50800 mixer (Dubuque, Iowa). Samples for the manual BCA protein assay and slurry turbidity measurements were analyzed using Shimadzu UV160U absorbance spectrophotometer (Kyoto, Japan). Chromatographic studies were conducted using an LDC CM3200 pump, a model 713 autosampler from Thermoseparations, and a Rheodyne 7126 six-port injection valve (Cotati, Calif.). An LDC SM3100X absorbance detector was used to monitor hemoglobin during its reversed-phase extraction. The extraction of fluorescein and elution of FITC-labeled BSA was examined with a Shimadzu RF-535 fluorescence detector.

Microcolumn Preparation. The diol-bonded, aldehyde-activated, and immobilized protein supports were prepared from Nucleosil Si-1000, as described previously. The microcolumns were packed using a calibrated injection loop and support slurry of known concentration. The concentration of each slurry was determined in advance by turbidity measurements at 800 nm versus standard solutions that contained known concentrations of the support and packing solvent.

The permeability studies were performed in triplicate using columns packed with diol-bonded silica of various pore sizes. The back pressure of these columns was measured as a function of flow rate between 0.0 and 3.0 mL/min. At each new flow rate the system was allowed to stabilize before the back pressure was measured.

Packing reproducibility was examined by optical microscopy and by performing protein assays on microcolumns containing immobilized hemoglobin silica. After packing these columns, their contents were removed and examined under a microscope or placed into a fixed volume of pH 7.0, 0.10 M phosphate buffer. The hemoglobin content of this latter suspension was determined by a BCA protein assay. After allowing the color of this assay to develop for 60 min, the support was removed from the reaction slurry by using a 0.45 micron syringe filter and the absorbance of the filtrate was measured at 562 nm.

Chromatographic Studies. All studies were performed at room temperature. The reversed-phase extraction of hemoglobin was studied using a 2.1 mm ID×1.0 cm column which contained a 1.1 mm layer of $C_{18}$ Nucleosil Si-100; diol-bonded sillica was used to fill the remainder of the column housing. A series of 10 μL injections of a 2 μg/mL hemoglobin solution were made onto this column in pH 7.0, 0.10 M phosphate buffer at effective residence times ranging from 1–600 ms. The amount of non-retained hemoglobin was measured at 428 nm and was compared to the signal obtained when no $C_{18}$ support was present in the chromatographic system.

The immunoaffinity support for the adsorption-limited studies was prepared by coupling anti-fluorescein antibodies to diol-bonded silica through the Schiff base method. Prior to coupling, these antibodies were incubated with fluorescein to protect their binding sites from inactivation during the immobilization reaction. The immobilized antibodies were later washed with pH 2.5, 0.10 M phosphate buffer to release the bound fluorescein. This immunoaffinity support was then placed into pH 7.0, 0.10 M phosphate buffer and used to pack a 545 μm thick layer within a 2.1 mm ID×1.0 cm column, with the remainder of the column containing diol-bonded silica. A series of 50 μL injections of 5.4 nM fluorescein were made onto this column at flow rates of 0.4–1.1 mL/min using pH 7.0, 0.10 M phosphate buffer as the application solvent. The amount of non-retained fluorescein was monitored by using on-line fluorescence detection with excitation and emission wavelengths of 488 and 520 nm, respectively. Between each injection, the column was washed with pH 2.5, 0.10 M phosphate buffer, followed by re-equilibration with the pH 7.0 application buffer. The relative amount of extracted fluorescein was determined by comparing the non-retained peak areas of the anti-fluorescein column to peak areas measured for the same samples when applied at identical flow rates to a column that contained only diol-bonded silica.

The immunoaffinity support for the chromatographic competitive binding immunoassay was prepared by adsorbing anti-BSA antibodies to a 2.1 mm ID×1.0 cm column that contained a 1.1 mm thick layer of an immobilized protein G support. Antibodies were placed onto this column by making two 50 μL injections of anti-BSA antiserum at a flow rate of 0.05 mL/min in pH 7.4, 0.10 M phosphate buffer. Samples containing FITC-labeled BSA and BSA were injected in the same buffer and the amount of non-retained labeled BSA was monitored through its fluorescence at excitation and emission wavelengths of 488 and 520 nm. The retained BSA and labeled BSA were later eluted with pH 2.5, 0.10 M phosphate buffer. The column was then re-equilibrated with pH 7.4, 0.10 M phosphate buffer before the next sample injection.

Example 1

Preparation of Microcolumns

One goal of this work was to decrease the residence times that could be obtained with HPLC columns while still allowing the use of these columns at standard flow rates. It is difficult to pack an ordinary chromatographic column with a length of less then a few millimeters, so a sandwich-based method was used instead. This was accomplished by employing a conventional HPLC pump and injection valve to apply slurry of one or more types of supports to a column. Table 1 shows the procedure used to make a typical column for this study. For convenience in handling and for protection of the stationary phase layer, the column was first filled partially with a biologically-inert material, such as diol-bonded silica. After this support had been placed into the column, the flow rate of the packing solvent was increased to ensure that this material was present in an even layer. A layer of the desired active support was next placed into the column in a similar manner to give a sandwich microcolumn. The length of this layer was determined by the concentration and volume of the injected support slurry and the number of injections that were made of this slurry. The remainder of the column was then filled with diol bonded silica or some other inert support to remove any dead space at the head of the column.

Figure 2:
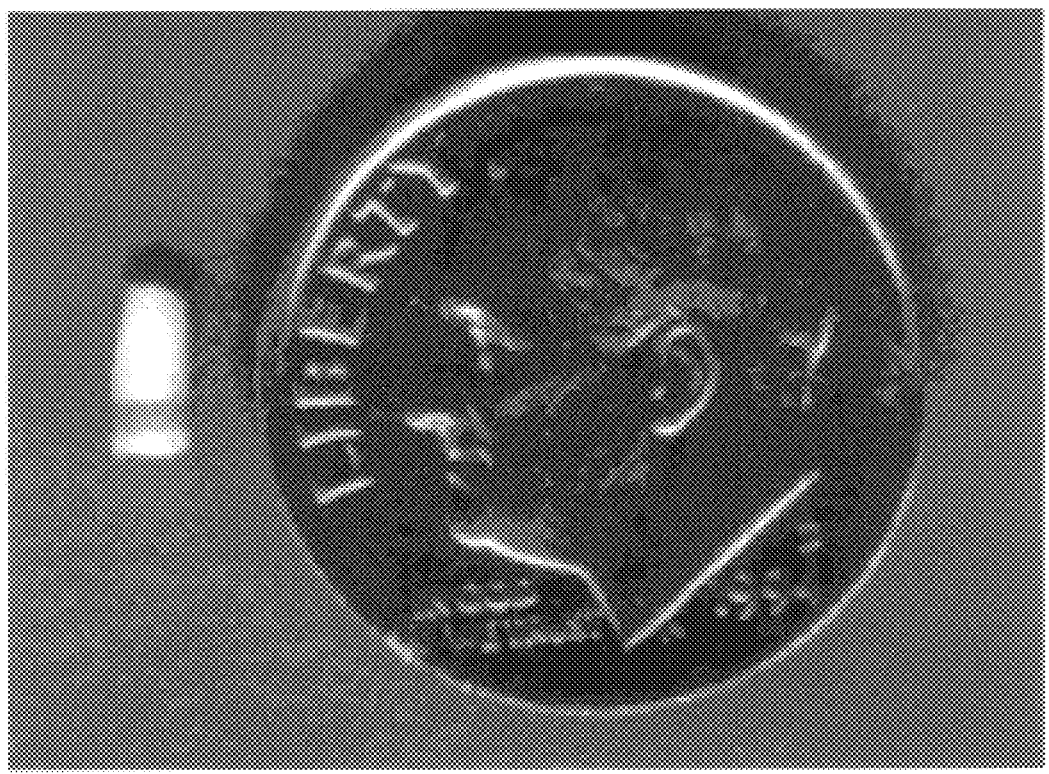
FIG. 2 depicts a typical microcolumn. This column was packed with Nucleosil Si-300 silica and later removed from its housing for the acquisition of this image. Immobilized hemoglobin silica, shown as the dark center band, was used to visualize the stationary phase layer after the column was unpacked. The total length of the column shown was 1.0 cm and the effective length of the stationary phase layer was 620 $\mu$m. The column diameter was 2.1 mm.

A picture of a typical microcolumn that was prepared for this study is shown in FIG. 2. The effective length ($L_{eff}$) and volume ($V_{eff}$) occupied by the stationary phase layer within such a column was adjusted by using the following equations, $$V_{eff} = N_{inj} V_{inj} C_s / \rho_s \quad (1)$$

$$L_{eff} = (N_{inj} V_{inj} \pi_s) / (pr^2 \rho_s) \quad (2)$$

Where $C_s$ is the concentration of the support in the injected slurry, $V_{inj}$ is the volume of this slurry which was applied with each injection, $N_{inj}$ is the total number of slurry injections that were made of the given support, $\rho_s$ is the packing density of the support within the column, and r is the internal radius of the column. An experimentally-measured packing density of 0.64 g/cm³ was used for the silica employed in this work and the calibrated injection volume was 152 μL. A total of 32 or 64 injections for a particular support was usually employed, as will be discussed later. The length of the support layer was varied by changing the density of its injected slurry. In the initial stages of this work, the final lengths of the support layers in the microcolumns were determined by using a colored support (as shown in FIG. 2) and optical microscopy to measure the thickness of this layer. In each case, the actual thicknesses of the stationary phase layers were found to agree within experimental error to the lengths that were estimated by using Eqn. 2.

The total length of all columns used in this work was 1.0 cm, which included both the stationary phase-coated support and all inert materials. However, the thickness of the stationary phase layer (referred to here as the microcolumn "length") ranged from 1.1 mm to 60 μm. Since these columns were packed with 5–7 μm silica particles, these microcolumns had effective lengths that were equal to only 9–157 particle diameters. Work with such small columns was possible because the separations that were to be performed with them were essentially irreversible under the time and solvent conditions that were considered in this study. This gave rise to extractions and assays, which generally involved the use of only single contacts between the retained molecules and the stationary phase. Several specific examples of such applications are provided below.

Example 2

Evaluation of Sandwich Microcolumns

The reproducibility of microcolumn packing was tested. One way this was done was by comparing the total protein content of several columns that had been packed with small layers of an immobilized hemoglobin support. When two injections of a 4.8 mg/mL slurry were made of this material, this delivered a 620 μm thick layer with a precision of approximately 20% (±1 RSD). This reproducibility was much worse than the precision of only a few percent that was observed for the protein assay itself, thus indicating that this variability was mainly due to the packing method. Several possible sources of this variability were considered to improve the reproducibility of the packing procedure. These sources included 1) potential changes in the slurry density between injections and 2) possible variations in the slurry volume that was applied with each injection onto the column.

To ensure that the slurry density remained constant over time, this density was routinely monitored by turbidity measurements and maintained by vigorous mixing of the slurry between injections. This resulted in slurry densities that showed less than a few percent variation over even a large series of injections. An approach was also developed for minimizing the effects of variations in the injection volume; this was done by using a large number of injections of dilute slurry suspensions to average out such effects and reduce their overall impact. FIG. 3 shows some results that were obtained by this technique for a 620 μm support layer. As can be seen from this plot, an increase in the number of slurry injections (with a corresponding decrease in slurry concentration) resulted in a significant improvement in the precision of the packing method. In this example a variation of less than 5% in support delivery was obtained when using 32 injections of a 0.3 mg/mL slurry. For longer microcolumns, an even better precision was obtained under comparable conditions; however, work with smaller column lengths required a greater number of injections to obtain similar results.

Microcolumns containing a colored support, like the hemoglobin silica shown in FIG. 2, were inspected by optical microscopy for their packing uniformity. It was found that columns containing support layers of 60 μm in length or greater gave level, well-defined boundaries. But attempts to pack even smaller columns gave rise to some edging effects in which the support layers were no longer packed evenly across the diameter of the column. In this case, the walls of the column contained a slightly larger layer of the colored support than the section in the center of the column. It is believed that this is due to the presence of some flow heterogeneity within the column during the packing procedure. Such an effect was not noticeable or significant in the longer microcolumns (effective lengths, 60 μm–1.1 mm) that were used in the remainder of this study.

Figure 4:
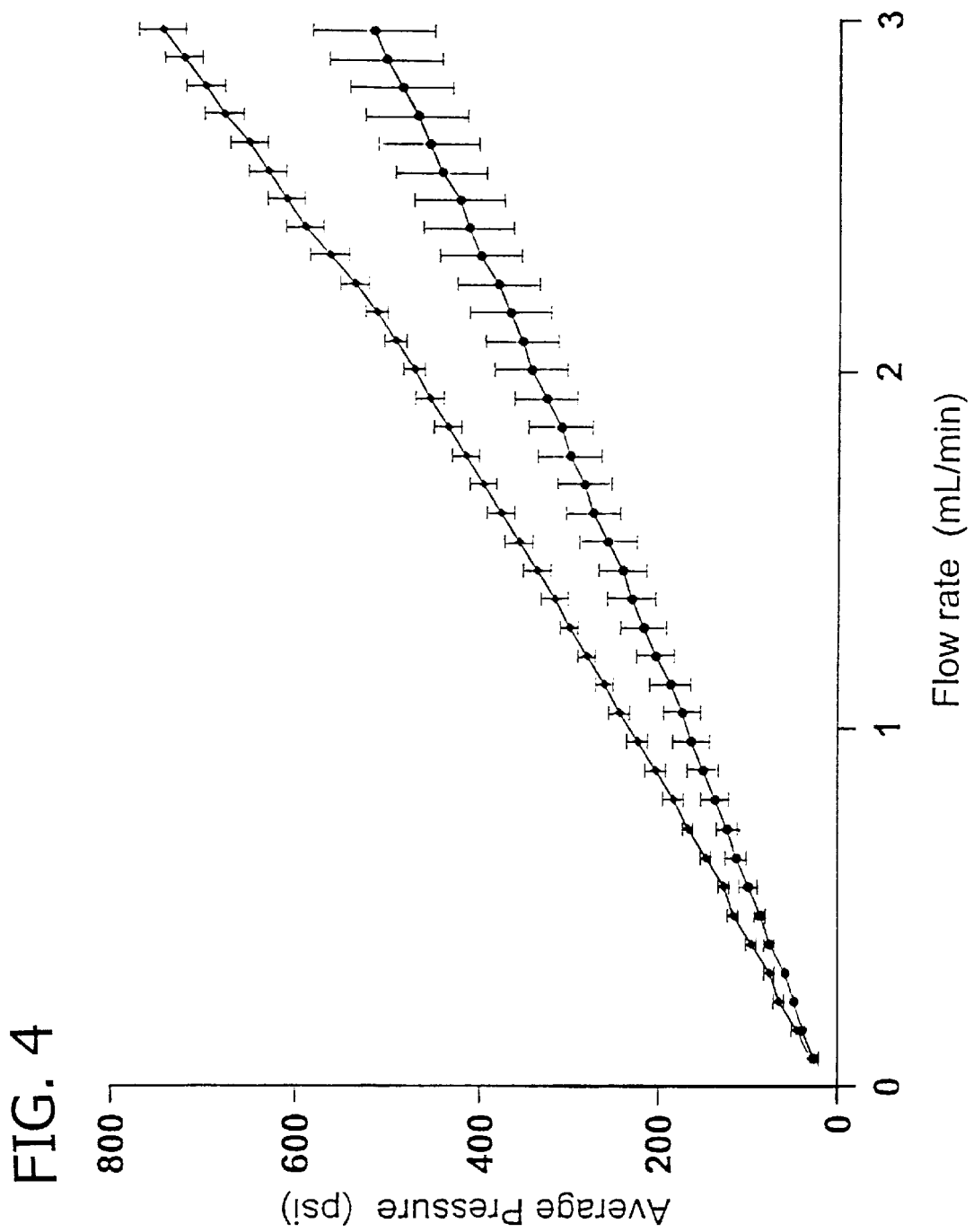
FIG. 4 depicts pressure versus flow rate for columns packed with Nucleosil Si-1000 [♦] or Nucleosil Si-300 [●] supports. These measurements were performed at room temperature using pH 7.0, 0.1 M potassium phosphate buffer as the mobile phase. The error bars shown about each point represent a range of ±1 SD for triplicate measurements.

Another series of studies were performed to determine the flow rates and column residence times that could be employed with the sandwich microcolumns. This required that some information be obtained on the permeability of these columns. This was done by packing several microcolumns with 7 μm diameter HPLC-grade silica that had nominal pore sizes of 300–4000 Å. These supports were chosen because they are commonly used for proteins and other biological molecules in HPLC. For each type of support, a plot was made of back pressure versus flow rate, as shown in FIG. 4. This type of plot was then analyzed by using the Darcy equation, $$\Delta P = (u_{mp} \epsilon_o \eta L) / B_o \quad (3)$$

where $U_{mp}$ is the linear velocity of the mobile phase, $\epsilon_o$ is the column's interstitial porosity, $\eta$ is the mobile phase viscosity, L is the total column length, $\Delta P$ is the change in pressure across the column, and $B_o$ is the specific permeability of the support within the column.

According to Eqn. 3, the overall permeability of the column ($B_o$) can be determined from the slope of plots like those in FIG. 4 by converting from flow rate to linear velocity and using the known or measured values of $\epsilon_o$, $\eta$ and L. The permeabilities that were measured for the sandwich microcolumns are given in Table 2 for several porous silica supports. Based on these values, the maximum usable flow rates for microcolumns packed with these materials were calculated to range from 12 to 17 mL/min at a back pressure of 3000 psi; in practice, an upper limit of 9–10 mL/min was actually observed because of some non-linearity that occurred in plots of back pressure versus flow rate when working at high flow rates (see upper plot in FIG. 4). However, work at flow rates below this range was more than adequate for this study since a typical 500 μm long×2.1 mm ID microcolumn allowed sample residence times of 40–80 ms to be obtained at 1–2 mL/min. As will be shown later, residence times as low as even 1–2 ms could be obtained by using shorter columns and/or higher flow rates for sample application.

Example 3

Extraction by Sandwich Microcolumns Under Adsorption-limited Conditions

Figure 5:
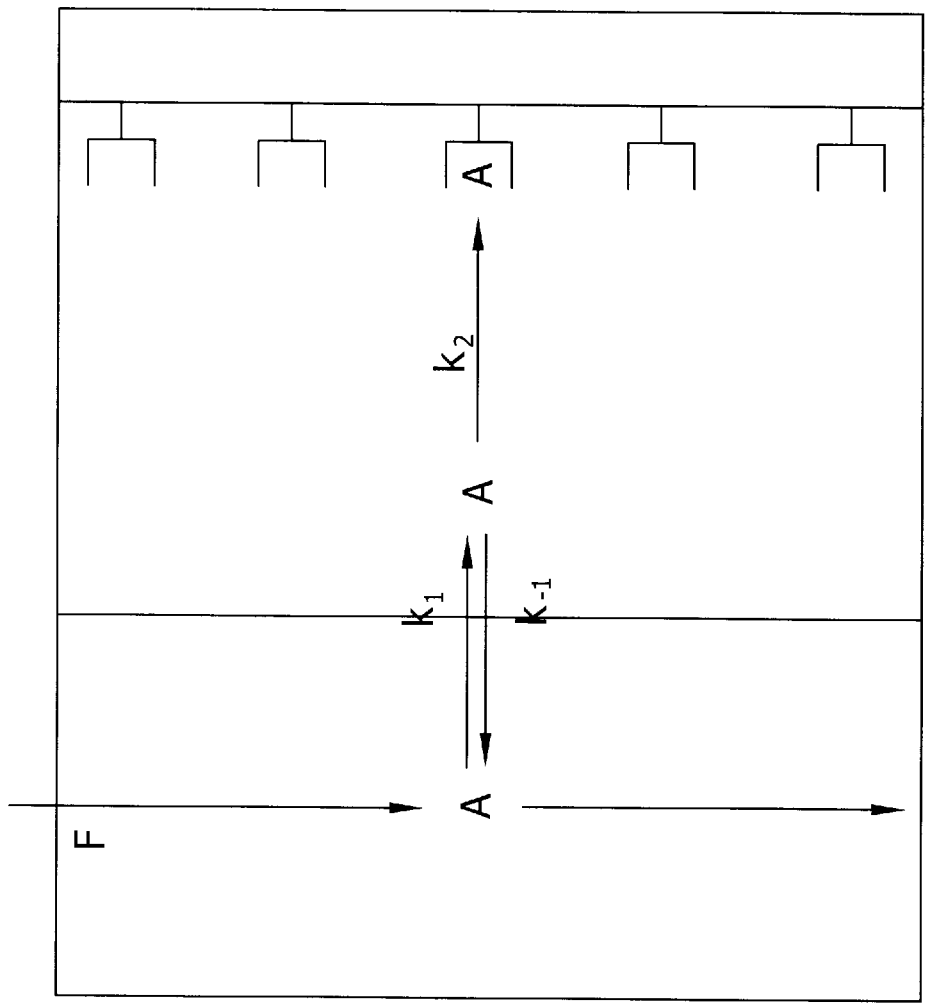
FIG. 5 depicts the general scheme used to represent analyte extraction by microcolumns. The forward and reverse mass transfer rate constants $k_1$ and $k_{-1}$ represent movement of the analyte (A) from the flowing mobile phase to stagnant mobile phase within the support. The second-order rate constant $k_2$ describes the actual adsorption of the analyte to the stationary phase. A reverse first-order rate constant for analyte desorption could also be included in this model ($k_{-2}$); however, this was not necessary in this current study since analyte binding to the column was essentially irreversible on the time scale of the extraction studies.

The next series of experiments considered the behavior of sandwich microcolumns in extractions performed in systems with either "diffusion-limited" or "adsorption-limited" kinetics for analyte retention. This was based on a model in which analyte interaction with the stationary phase was viewed as consisting of two distinct steps (see FIG. 5): 1) movement of the analyte to the surface of the stationary phase by diffusion, and 2) adsorption or interaction of the analyte with the stationary phase. The term "diffusion-limited kinetics" is used here to refer to a system in which the overall rate of analyte binding to the stationary phase is dictated by how fast the analyte can get to the stationary phase from the flow mobile phase. For the model shown in FIG. 5, this occurs when the rate constant $k_2$ is much larger than $k_1$ or $k_{-1}$. The opposite situation (adsorption-limited kinetics) occurs when $k_1$ and $k_{-1}$ are much larger than $k_2$. In this situation, the analyte gets to the stationary phase at a rate that is much faster than analyte-stationary phase binding, thus making this second process the rate-limiting step in retention.

The first case, which was examined, was that of a system with adsorption-limited kinetics. This was accomplished by injecting a small analyte (fluorescein) onto a column that contained anti-fluorescein antibodies attached to HPLC-grade silica. Previous studies have shown that antibody-antigen systems such as this tend to display adsorption-limited kinetics when the antibody is part of an HPLC column. Each fluorescein sample was first injected in triplicate at various flow rates onto an inert column containing only diol-bonded silica, to which fluorescein does not bind, in order to determine the total expected peak area. The same sample was then applied to a sandwich microcolumn of the same overall size as the inert control column, but which now contained a well-defined layer of anti-fluorescein antibodies. The degree of extraction was then determined by comparing the size of the non-retained peaks for fluorescein on the microcolumn to those measured at the same flow rates on the control column.

Figure 6:
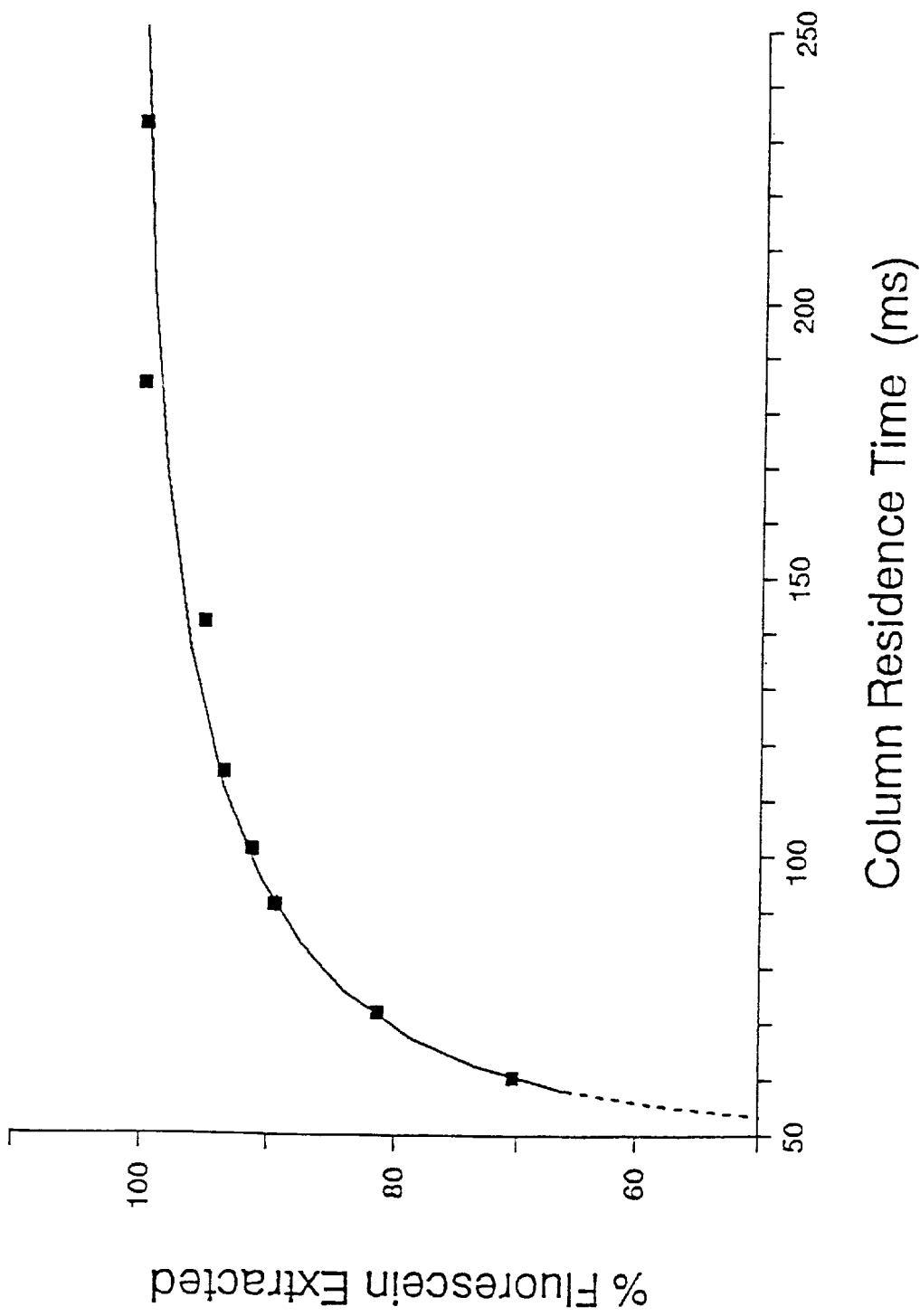
FIG. 6 depicts extraction of fluorescein using an anti-fluorescein immunoaffinity support. Microcolumns varying in lengths from 124 $\mu$m to 620 $\mu$m were used for this study along with various flow rates to adjust the column residence times.

The results of this experiment are summarized in FIG. 6. It was found that greater than 95% extraction of fluorescein could be obtained in as little as 100–120 ms with sandwich microcolumns. Previous studies with antibodies attached to low-performance agarose supports have reported greater than 95% binding in roughly 100 s or 40% extraction of analytes in 2 s, while antibodies attached to HPLC supports have been shown to give quantitative extraction in as little as 6 s. However, this present study is the first report in which quantitative binding with immunoaffinity supports has been noted in the millisecond time range. Similar studies were conducted with sandwich microcolumns and antibodies directed against other analytes. For instance, the analytes L-thyroxine and warfarin have also been found to give quantitative extraction in only 60–150 ms by such columns.

When attempting this type of rapid extraction, it is necessary to consider the amount of stationary phase that is actually present in the column for analyte retention. Increasing the amount of stationary phase per unit volume not only helps avoid column overloading, but in an adsorption-limited system this also helps to speed the net rate of retention by increasing the probability that an analyte will encounter an unoccupied binding site as it approaches the stationary phase. Typically, immunoaffinity extractions use a large excess of antibodies to help avoid these problems. But this can be more difficult to attain in microcolumns, where the space available for the stationary phase is minimal. To address this, the anti-fluorescein antibodies used in this study were immobilized under conditions which have previously been shown to maximize the density of antibodies on HPLC-grade silica supports. This provided an amount of antibodies in the anti-fluorescein microcolumns which was roughly 2000 to 3000-times greater than the moles of fluorescein that were injected. As can be seen from FIG. 6, this level was more then sufficient to allow quantitative extractions of fluorescein to be achieved in the sub-second time domain.

Example 4

Extraction by Sandwich Microcolumns Under Diffusion-limited Conditions

The second type of kinetic case considered was the use of sandwich microcolumns to extract analytes under diffusion-limited conditions. An example of such a system is the retention of a protein like hemoglobin by a reversed phase support. This was studied by packing a sandwich microcolumn that contained a 1.1 mm layer of $C_{18}$ silica between layers of diol-bonded silica. The degree of extraction of hemoglobin samples was estimated by making a continuous series of protein injections, with no elution step in between, until the column was saturated with hemoglobin. All of the peak areas were then compared to those for peaks which were generated after column saturation. A similar comparison was made between the peaks measured on the $C_{18}$ microcolumn and those that were obtained for the same samples on an inert control column that contained only diol-bonded silica.

Figure 7:
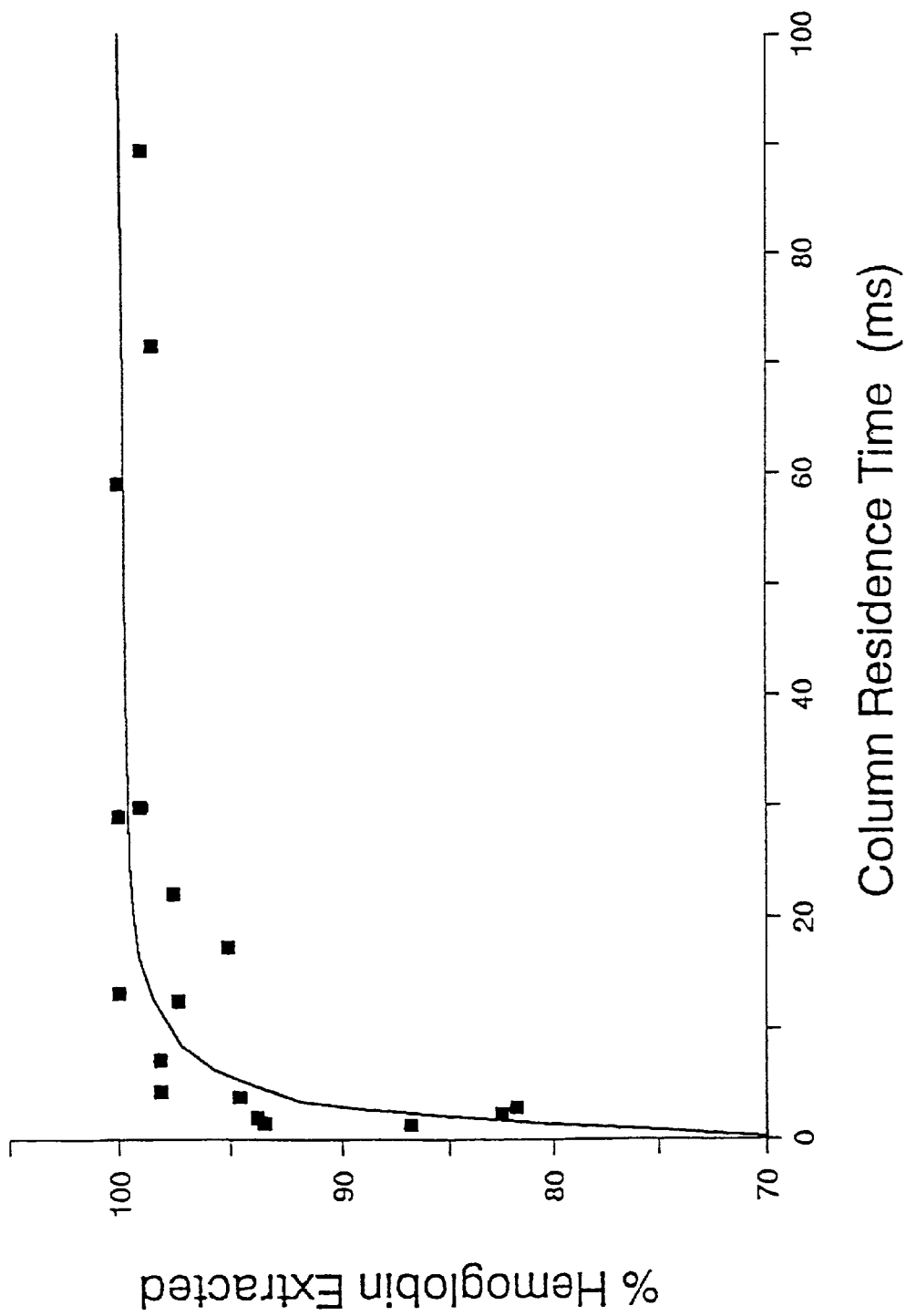
FIG. 7 depicts extraction of hemoglobin using a reversed-phase chromatographic support. Microcolumns varying in lengths from 62 $\mu$m to 620 $\mu$m were used for this study along with various flow rates to adjust the column residence times.

The data that were obtained with this system are illustrated in FIG. 7. It was found that up until the point of column saturation (which occurred after about twenty-four 100 $\mu$L injections of 2 mg/mL hemoglobin) greater than 95% of the injected hemoglobin was extracted at residence times as short as 4 ms. This was followed by a fairly sharp decrease in extraction efficiency at shorter times (i.e., 1–2 ms). This extraction rate was much faster than what was observed in FIG. 6 for the fluorescein/anti-fluorescein system. One reason for this is that the fluorescein system had adsorption-limited kinetics in which retention was limited by the rate at which the analyte could reach unoccupied antibody sites with a proper orientation for binding. In contrast to this, the binding of hemoglobin to $C_{18}$ silica is a much faster, but less specific, diffusion-limited process that involves a greater number of potential binding regions and in which many more collisions of hemoglobin with the stationary phase result in analyte retention.

Example 5

Use of Sandwich Microcolumns in Chromatographic Immunoassays

The last series of studies considered the use of sandwich microcolumns in a chromatographic immunoassay. This type of assay uses immobilized antibodies or antigens as part of a chromatographic system for the fast and selective determination of analytes. The most common format for such an assay is the competitive binding mode. In this format, analyte in the sample is incubated with a fixed amount of a labeled analyte analog and is applied to a column that contains a limited amount of antibodies that can bind to both of these species. This is most often done by simultaneously injecting the analyte and its labeled analog onto the column, but sequential injection can also be employed. The antibody-bound fraction of both compounds is then separated from the fraction that remains free in solution. From this, the amount of labeled analyte that was in the free or bound fraction can be determined, thus providing an indirect measure of how much analyte was in the original sample.

Sandwich microcolumns are attractive for use in such assays because they provide a convenient way of placing a small amount of antibodies into a column while still allowing work to be performed at flow rates and column residence times that allow a competition to be established between the analyte and its labeled analog. In addition, the use of microcolumns will minimize the surface area to which the analyte and label are exposed. This should help reduce non-specific binding, which is often a limiting factor in determining the lower limit of detection that can be obtained in immunoassays.

Figure 8:
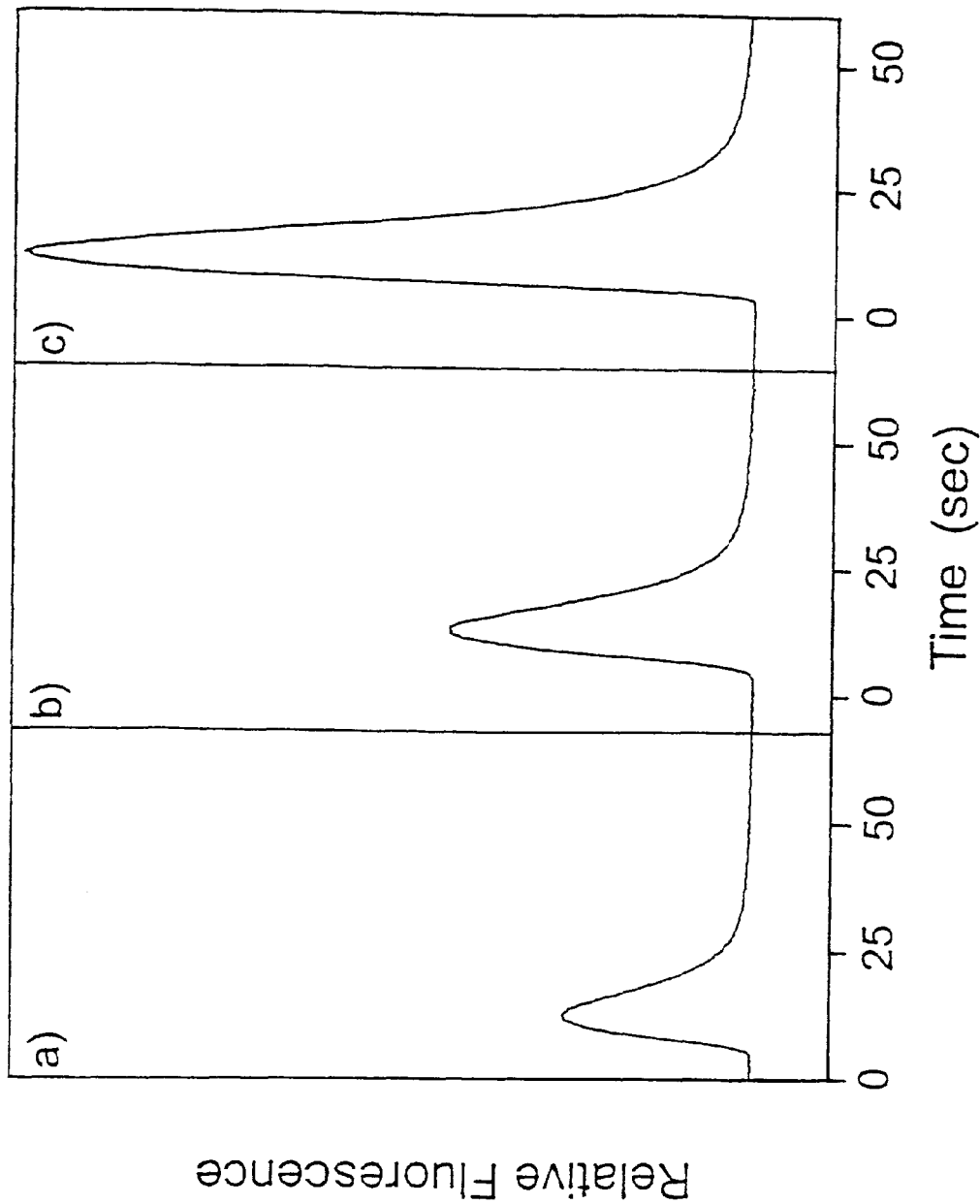
FIG. 8 depicts a competitive binding immunoassay for albumin performed on a column that contained anti-albumin antibodies as the stationary phase. The column was prepared and sample injections were performed as described in the text. Sample injection took place at 0 min in each plot. The concentration of FITC-BSA in each sample was 1.6 µM. The concentrations of non-labeled BSA were (from left-to-right) 0, 17.9 and 88.8 µM, respectively.

A chromatographic competitive binding immunoassay with microcolumns was developed by using the competition of labeled and non-labeled BSA as a model. Anti-BSA antibodies were first adsorbed to a protein G microcolumn to form an immunoaffinity stationary phase. Various mixtures of FITC-labeled BSA and non-labeled BSA were then injected onto this column, with the non-retained labeled BSA being monitored by an on-line fluorescence detector. Some typical chromatograms obtained by this method are shown in FIG. 8. The sample on the left contained only a solution of the labeled BSA, while the second and third samples to the right contained the same amount of labeled BSA plus either a 10-or 50-fold excess of normal BSA.

An 80% extraction of labeled BSA was achieved in the sample containing only this labeled compound. Injection of this label plus a 10-fold excess of non-labeled BSA yielded a 15% decrease in the binding of labeled BSA, and injection of the labeled BSA plus a 50-fold excess of non-labeled BSA gave a 65% decrease in binding (see FIG. 8). It is this inverse relationship between binding of the labeled analog and the concentration of the unlabeled analyte, which can be used for analyte measurements. For each injected solution, the amount of time the sample was in contact with the immunoaffinity support was approximately 180 ms. However, a signal was not observed until about 5–25 s after injection due to the additional time that was required for the sample to pass out of the injection loop and through the column, connecting tubing and detector. These results clearly indicate that a sandwich microcolumn can be used to perform competitive binding immunoassays on very short time scales. This approach is not limited to BSA, but could also be employed with any other compounds for which antibodies and an appropriately labeled analog are available.

In light of the detailed description of the invention and the examples presented above, it can be appreciated tha the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventor does not intend to be bound by those conclusions and functions, but puts them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. A method of loading a microcolumn comprising an active layer and an inert layer, the active layer being capable of separating an analyte from a sample, the method comprising:
    (a) introducing the active layer into the microcolumn by a plurality of injections such that the active layer is capable of separating the analyte from the sample within the millisecond time domain; and
    (b) introducing the inert layer.

2. The method of claim 1 wherein the active layer is introduced into the microcolumn as slurry, the slurry comprising particles that form the active layer and a packing solvent.

3. The method of claim 2 wherein the particles are selected from the group of materials consisting of porous glass, nonporous glass, silica, inorganic supports, carbohydrate based supports, and polymeric supports.

4. The method of claim 2 wherein the flow rate of slurry during injection is varied such that the flow rate is increased at the beginning and end of the introduction of each layer loaded into the microcolumn.

5. The method of claim 2 wherein the pressure during slurry injection is varied such that the pressure is increased at the beginning and end of the introduction of each layer loaded into the microcolumn.

6. The method of claim 1 wherein the inert layer is introduced into the microcolumn as slurry, the slurry comprising particles that form the inert layer and a packing solvent.

7. The method of claim 6 wherein the particles are selected from the group of materials consisting of diol-bonded silica, diol-bonded glass beads, agarose beads, hydroxylated perfusion media, and glycol coated perfusion media.

8. The method of claim 6 wherein the particles comprise diol-bonded silica.

9. The method of claim 6 wherein the particles of the inert layer, when the column is in use do not substantially interact with the analyte.

10. The method of claim 1 wherein the number of injections to introduce the active layer into the microcolumn is from about 30 to about 40 when the layer length is from about 100 to about 500 microns.

11. The method of claim 1 wherein the number of injections to introduce the active layer into the microcolumn is from about 60 to about 80 when the layer length is from about 60 to about 100 microns.

12. The method of claim 1 wherein the active layer is introduced into the microcolumn as a slurry, the slurry comprising particles that form the active layer and a packing solvent.

13. The method of claim 12 wherein the slurry density is from about 0.1 to about 20 milligrams of particles per milliliter of packing solvent.

14. The method of claim 12 wherein the slurry density is from about 1 to about 5 milligrams of particles per milliliter of packing solvent.

15. The method of claim 14 wherein a consistent slurry density is maintained during injection by mixing the slurry between injections and measuring the turbidity of the slurry at a wavelength of approximately 800 nm.

16. The method of claim 1 wherein the number of injections to introduce the active layer into the microcolumn is from about 10 to about 100.

17. The method of claim 1 wherein the particles are introduced into the column in a uniform manner.

18. The method of claim 1 wherein the active layer is from about 10 microns to about 1.1 millimeters in length.

19. The method of claim 1 wherein the active layer is not less than about 60 microns in length.

20. The method of claim 1 wherein the inert layer is at least about 1 to about 5 times the length of the active layer.

* * * * *

UNITED STATES PATENT AND TRADEMARK OFFICE
CERTIFICATE OF CORRECTION

| | |
|---|---|
| PATENT NO. | : 6,500,671 B2 |
| APPLICATION NO. | : 09/776800 |
| DATED | : December 31, 2002 |
| INVENTOR(S) | : David S. Hage et al. |

It is certified that error appears in the above-identified patent and that said Letters Patent is hereby corrected as shown below:

Column 1 at line 5 insert the following phrase, --This invention was made with government support under grant GM044931 awarded by the National Institute of Health. The government has certain rights in the invention.--

Signed and Sealed this

Twenty-sixth Day of February, 2008

JON W. DUDAS
*Director of the United States Patent and Trademark Office*